(12) United States Patent
Igarashi (10) Patent No.: US 10,739,576 B2
(45) Date of Patent: Aug. 11, 2020

(54) IMAGING APPARATUS, ENDOSCOPIC SYSTEM, AND IMAGING APPARATUS MANUFACTURING METHOD

(71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 386 days.

(21) Appl. No.: 15/802,512

(22) Filed: Nov. 3, 2017

(65) Prior Publication Data

US 2018/0067298 A1 Mar. 8, 2018

Related U.S. Application Data

(63) Continuation of application No. PCT/JP2015/063681, filed on May 12, 2015.

(51) Int. Cl.
*G02B 23/24* (2006.01)
*H04N 5/225* (2006.01)
(Continued)

(52) U.S. Cl.
CPC ........ *G02B 23/2407* (2013.01); *A61B 1/0011* (2013.01); *A61B 1/00096* (2013.01);
(Continued)

(58) Field of Classification Search
CPC combination set(s) only.
See application file for complete search history.

(56) References Cited

U.S. PATENT DOCUMENTS 4,832,003 A * 5/1989 Yabe ............... A61B 1/051
348/65
5,734,418 A * 3/1998 Danna ............. A61B 1/05
348/65
(Continued)

FOREIGN PATENT DOCUMENTS

CN 107205614 A 9/2017
JP S55-052010 A 4/1980
(Continued)

OTHER PUBLICATIONS

Chinese Office Action dated Jul. 1, 2019 issued in Chinese Patent Application No. 201580079795.2.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An imaging apparatus includes: an optical system configured to collect incident light; an imaging element including a light receiver configured to receive light input from the optical system and perform photoelectric conversion to generate an electrical signal; and an optical system adhesive layer configured to bond the optical system to a principal surface of the imaging element where the light receiver is provided. The optical system adhesive layer is a photosensitive transparent adhesive for which patterning is performed through a photolithography process and which has a function of determining a position of the optical system relative to the light receiver.

12 Claims, 11 Drawing Sheets

(51) Int. Cl.
*A61B 1/05* (2006.01)
*G02B 7/02* (2006.01)
*A61B 1/00* (2006.01)
*G02B 7/00* (2006.01)
*A61B 1/04* (2006.01)
*A61B 1/045* (2006.01)

(52) U.S. Cl.
CPC .............. *A61B 1/042* (2013.01); *A61B 1/051* (2013.01); *G02B 7/00* (2013.01); *G02B 7/025* (2013.01); *G02B 23/2423* (2013.01); *H04N 5/225* (2013.01); *H04N 5/2254* (2013.01); *A61B 1/045* (2013.01); *H04N 2005/2255* (2013.01)

(56) References Cited

U.S. PATENT DOCUMENTS

| | | | | |
|---|---|---|---|---|
| 5,862,283 | A * | 1/1999 | Trott | G02B 6/4219 385/147 |
| 6,204,966 | B1 | 3/2001 | Steinhuber | |
| 6,811,853 | B1 * | 11/2004 | Sherrer | B81C 1/00396 216/2 |
| 7,616,250 | B2 * | 11/2009 | Watanabe | H01L 27/14618 257/432 |
| 2004/0027675 | A1 * | 2/2004 | Wu | B82Y 30/00 359/619 |
| 2005/0182299 | A1 * | 8/2005 | D'Amelio | A61B 1/00096 600/175 |
| 2007/0244364 | A1 * | 10/2007 | Luanava | A61B 1/0008 600/160 |
| 2008/0036020 | A1 * | 2/2008 | Ko | H01L 27/14621 257/431 |
| 2008/0080028 | A1 * | 4/2008 | Bakin | G06T 1/0007 358/514 |
| 2009/0040345 | A1 * | 2/2009 | Fukuyoshi | G02B 5/201 348/273 |
| 2009/0224344 | A1 * | 9/2009 | Huang | H01L 27/14618 257/432 |
| 2010/0073470 | A1 * | 3/2010 | Takasaki | A61B 1/053 348/76 |
| 2012/0220825 | A1 * | 8/2012 | Kimura | A61B 1/051 600/109 |
| 2012/0253129 | A1 | 10/2012 | Kitano | |
| 2013/0120647 | A1 * | 5/2013 | Negishi | G02B 7/022 348/374 |
| 2013/0201143 | A1 * | 8/2013 | Han | G06F 3/042 345/173 |
| 2013/0265459 | A1 * | 10/2013 | Duparre | H04N 5/23238 348/218.1 |
| 2013/0321581 | A1 * | 12/2013 | El-Ghoroury | H04N 5/225 348/46 |
| 2013/0333843 | A1 * | 12/2013 | Kim | B29C 65/80 156/362 |
| 2014/0118516 | A1 * | 5/2014 | Suzuki | H04N 5/2254 348/65 |
| 2015/0065798 | A1 * | 3/2015 | Kuroda | A61B 1/00096 600/109 |
| 2015/0245763 | A1 * | 9/2015 | Kido | A61B 1/0011 600/109 |
| 2015/0286033 | A1 * | 10/2015 | Osborne | G02B 13/0015 348/345 |
| 2016/0260761 | A1 * | 9/2016 | Jun | H01L 27/14618 |
| 2016/0338574 | A1 * | 11/2016 | Fujimori | G02B 23/2423 |
| 2017/0038552 | A1 * | 2/2017 | Georgiev | G06T 7/0004 |
| 2017/0322411 | A1 | 11/2017 | Igarashi | |

FOREIGN PATENT DOCUMENTS

| | | |
|---|---|---|
| JP | H07-191267 A | 7/1995 |
| JP | H08-327914 A | 12/1996 |
| JP | H09-262207 A | 10/1997 |
| JP | 2000-271066 A | 10/2000 |
| JP | 2001-502819 A | 2/2001 |
| JP | 2002-045333 A | 2/2002 |
| JP | 2005-309095 A | 11/2005 |
| JP | 2007-212673 A | 8/2007 |
| JP | 2012-200480 A | 10/2012 |
| JP | 2015-042257 A | 3/2015 |
| JP | 2015-073537 A | 4/2015 |
| JP | 2015-165847 A | 9/2015 |
| WO | WO 2015/133254 A1 | 9/2015 |

OTHER PUBLICATIONS

Japanese Office Action dated Apr. 2, 2019 in Japanese Patent Application No. 2017-517529.
International Search Report dated Aug. 18, 2015 issued in PCT/JP2015/063681.

* cited by examiner

IMAGING APPARATUS, ENDOSCOPIC SYSTEM, AND IMAGING APPARATUS MANUFACTURING METHOD

CROSS-REFERENCE TO RELATED APPLICATIONS

This application is a continuation of PCT international application Ser. No. PCT/JP2015/063681 filed on May 12, 2015 which designates the United States, incorporated herein by reference.

BACKGROUND

1. Technical Field

The disclosure relates to an imaging apparatus that is provided at a distal end of an insertion portion of an endoscope to be inserted in a subject and captures an image of an inside of the subject, an endoscopic system including the imaging apparatus, and an imaging apparatus manufacturing method.

2. Related Art

In the related art, endoscopic systems have been widely used for various examinations, in a medical field and an industrial field. Among them, endoscopic systems for medical use enable observations or the like of a suspected region by inserting, into a subject such as a patient, an elongated flexible insertion portion having a distal end portion in which a built-in imaging apparatus is provided. In this kind of endoscopic system, it is desired to miniaturize the insertion portion in consideration of ease of introduction into the subject.

In general, an imaging apparatus used in an endoscopic system is configured such that an outer peripheral portion of an objective lens serving as an objective optical system is held by a frame member (lens barrel) made of metal, so that positions of the objective lens in a radial direction and an optical axis direction are determined. As a technique for miniaturizing an insertion portion provided with a built-in imaging apparatus, there has been disclosed an endoscope imaging apparatus configured such that an interval in an optical path direction is provided on a member (lens barrel holding member) that holds a frame member (lens barrel) of an objective optical system, an outer peripheral surface of the interval portion is cut, and then the lens barrel holding member is arranged close to an upper surface side of a solid state image sensor so that the height dimension of the endoscope imaging apparatus is reduced (for example, see JP 2000-271066 A and JP 2002-45333 A).

SUMMARY

In some embodiments, an imaging apparatus includes: an optical system configured to collect incident light; an imaging element including a light receiver configured to receive light input from the optical system and perform photoelectric conversion to generate an electrical signal; and an optical system adhesive layer configured to bond the optical system to a principal surface of the imaging element where the light receiver is provided. The optical system adhesive layer is a photosensitive transparent adhesive for which patterning is performed through a photolithography process and which has a function of determining a position of the optical system relative to the light receiver.

In some embodiments, an endoscopic system configured to be inserted in a living body and capture an image of an inside of the living body is provided. The endoscopic system includes: an endoscope including the imaging apparatus at a distal end portion of the endoscope.

In some embodiments, an imaging apparatus manufacturing method according to the disclosure includes: forming a layer of an optical system adhesive layer made of a photosensitive transparent adhesive on a wafer where a plurality of light receivers are provided; performing patterning on a portion of the optical system adhesive layer through a photolithography process, the portion being a portion on which an optical system that collects incident light is arranged; performing dicing on the wafer to obtain individual pieces of imaging elements; determining a position of the optical system on an imaging element by using the optical system adhesive layer as a position determination unit; and then connecting the optical system onto the imaging element.

The above and other features, advantages and technical and industrial significance of this disclosure will be better understood by reading the following detailed description of presently preferred embodiments of the disclosure, when considered in connection with the accompanying drawings.

DETAILED DESCRIPTION

Reference will be made below to an endoscopic system including an imaging apparatus as modes for carrying out the disclosure (hereinafter, referred to as "embodiment(s)"). The disclosure is not limited by the embodiments. The same reference signs are used to designate the same elements throughout the drawings. Note that the drawings are only schematic, and a relationship between a thickness and a width of each member, a ratio of each member, or the like are different from actual ones. Different drawings may include parts with dimensions or ratios being different from one another.

First Embodiment

Figure 1:
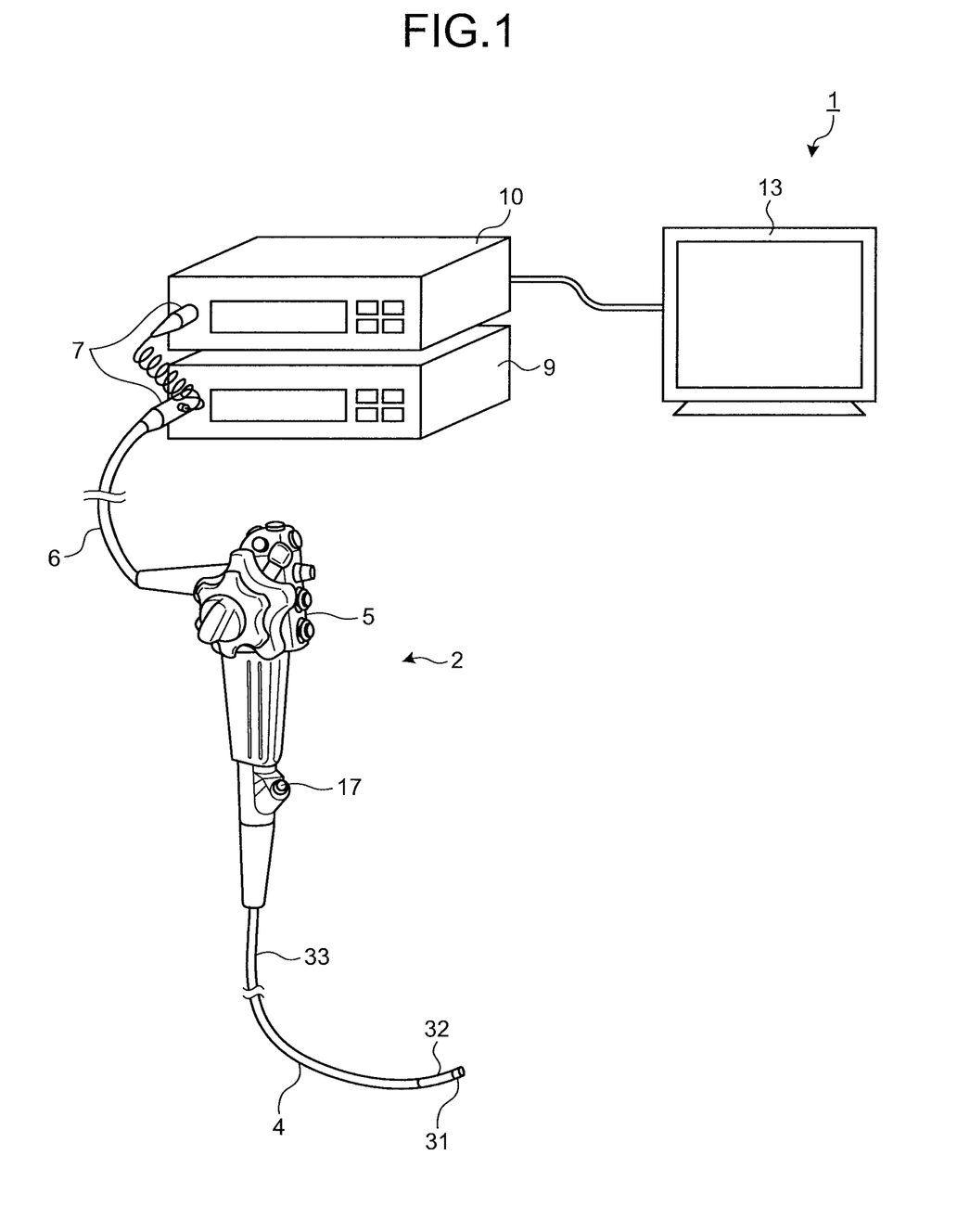
FIG. 1 is a schematic view of an overall configuration of an endoscopic system according to an embodiment of the disclosure.

FIG. 1 is a schematic view of an overall configuration of an endoscopic system according to an embodiment of the disclosure. As illustrated in FIG. 1, an endoscopic system 1 includes an endoscope 2, a universal code 6, a connector 7, a light source device 9, a processor (control device) 10, and a display device 13.

The endoscope 2 captures an in-vivo image of a subject and outputs an imaging signal by inserting an insertion portion 4 into the subject. An electric cable bundle inside the universal code 6 is extended to a distal end of the insertion portion 4 of the endoscope 2 and connected to an imaging apparatus provided at a distal end portion 31 of the insertion portion 4.

The connector 7 is provided at a proximal end of the universal code 6, is connected to the light source device 9 and the processor 10, performs predetermined signal processing on an imaging signal output from the imaging apparatus at the distal end portion 31 connected to the universal code 6, and performs analog-to-digital conversion (A/D conversion) on the imaging signal to output an image signal.

The light source device 9 is configured by using, for example, a white LED. Pulsed white light emitted by the light source device 9 passes through the connector 7 and the universal code 6 to serve as illumination light to irradiate an object from the distal end of the insertion portion 4 of the endoscope 2.

The processor 10 performs predetermined image processing on the image signal output from the connector 7, and controls the entire endoscopic system 1. The display device 13 displays the image signal processed by the processor 10.

An operating unit 5, on which various buttons or knobs for operating an endoscope function are provided, is connected to a proximal end side of the insertion portion 4 of the endoscope 2. A treatment tool insertion opening 17 for inserting a treatment tool such as a biopsy forceps, an electric scalpel, or an inspection probe into a body cavity of a subject is provided in the operating unit 5.

The insertion portion 4 includes the distal end portion 31 at which the imaging apparatus is provided, a bendable portion 32 that is continuously provided at a proximal end side of the distal end portion 31 and that is bendable in a plurality of directions, and a flexible tube portion 33 that is continuously provided at the proximal end side of the bendable portion 32. A bending tube 34 provided inside the bendable portion 32 (see FIG. 2) is bent by an operation on a bending operation knob provided on the operating unit 5, and is bendable in, for example, four directions including upward, downward, leftward, and rightward directions in accordance with pulling and loosening of a bending wire inserted in the insertion portion 4.

A light guide (not illustrated) that delivers illumination light from the light source device 9 is arranged on the endoscope 2, and an illumination lens (not illustrated) is arranged at an emission end at which the illumination light is emitted through the light guide. The illumination lens is provided at the distal end portion 31 of the insertion portion 4, and the illumination light is emitted toward a subject.

Figure 2:
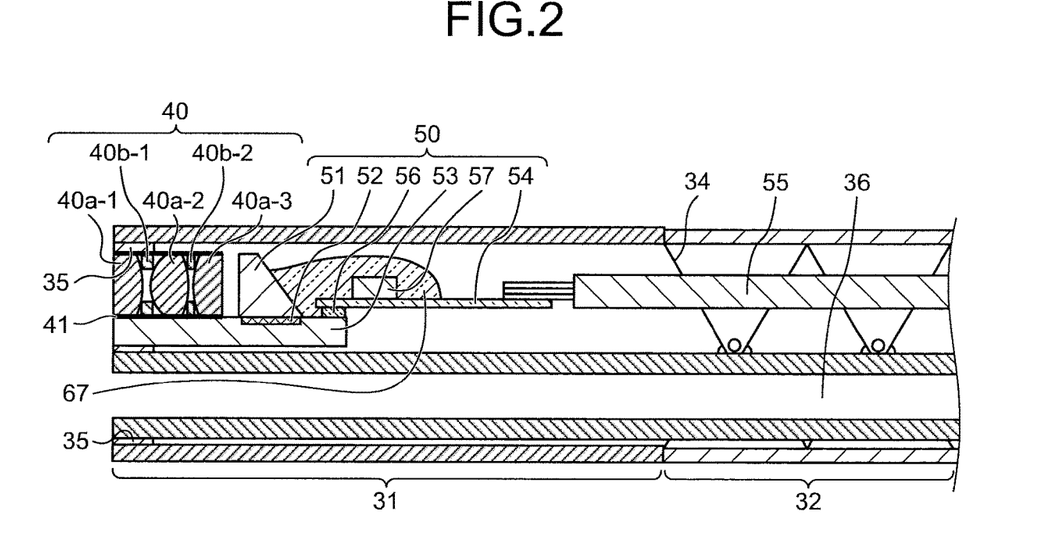
FIG. 2 is a partial cross-sectional view on a vertical plane parallel to an optical axis direction of a distal end of an endoscope illustrated in FIG. 1.

Next, a configuration of the distal end portion 31 of the endoscope 2 will be described in detail. FIG. 2 is a partial cross-sectional view on a vertical plane parallel to an optical axis direction of the distal end of the endoscope 2 illustrated in FIG. 1. In FIG. 2, the distal end portion 31 of the insertion portion 4 of the endoscope 2 and a part of the bendable portion 32 are illustrated.

As illustrated in FIG. 2, the bendable portion 32 is bendable in the four directions such as the upward, downward, leftward, and rightward directions in accordance with pulling and loosening of the bending wire inserted in the bending tube 34. An imaging apparatus 100 is provided in the upper part of the inside of the distal end portion 31 that is provided in an extending manner at a distal end side of the bendable portion 32, and a treatment tool channel 36 through which various treatment tools are extended is provided in the lower part.

The imaging apparatus 100 includes a lens unit 40 and an imaging unit 50 arranged at a proximal end side of the lens unit 40. An edge side of an imaging element, which will be described later, is bonded to the inside of the distal end portion 31 with an adhesive. The distal end portion 31 is made of a rigid member for forming an internal space in which the imaging apparatus 100 is housed. An outer peripheral portion of a proximal end of the distal end portion 31 is covered with a pliable covering tube (not illustrated). A member on a proximal end side of the distal end portion 31 is made of a flexible member such that the bendable portion 32 can be bent.

The lens unit 40 includes a plurality of objective lenses 40a-1 to 40a-3, spacers 40b-1 and 40b-2 arranged between the plurality of objective lenses 40a-1 to 40a-3, a diaphragm member (not illustrated), and a lens frame 41 that supports the plurality of objective lenses 40a-1 to 40a-3 or the like. The lens unit 40 is fixed to the distal end portion 31 by being inserted and fitted to be fixed to a distal end fixing portion 35 inside the distal end portion 31.

The imaging unit 50 includes a prism 51 that reflects light output through the objective lenses 40a-1 to 40a-3 of the lens unit 40, and an imaging element 53 including a light receiver 52 that receives the light reflected by the prism 51 and that performs photoelectric conversion to generate an electrical signal. The imaging element 53 is a transverse-mount type in which a principal surface, on which the light receiver 52 is provided, is arranged parallel (horizontally) to the optical axes of the objective lenses 40a-1 to 40a-3, and the prism 51 is arranged on the light receiver 52. A flexible printed board 54, to which a signal cable 55 is connected, is connected to a proximal end of the imaging element 53. An electronic component 57 for driving the imaging element 53, or the like is mounted on the flexible printed board 54. The imaging element 53 in the first embodiment of the disclosure is a charge coupled device (CCD) type or complementary metal oxide semiconductor (CMOS) type semiconductor imaging element.

A proximal end of the signal cable 55 extends in a proximal end direction of the insertion portion 4. The signal cable 55 is arranged by being inserted in the insertion portion 4, and is extended to the connector 7 through the operating unit 5 and the universal code 6 illustrated in FIG. 1.

Light incident on the distal end portion 31 is collected by the objective lenses 40a-1 to 40a-3, and is incident on the prism 51. The light receiver 52 receives light emitted from the prism 51, and converts the received light to an imaging signal. The imaging signal passes through the signal cable 55 connected to the flexible printed board 54 and the connector 7, and is output to the processor 10. In the descriptions of the present application, a side of the distal end portion 31 on which the light is incident, that is, a side on which the objective lenses 40a-1 to 40a-3 are arranged, will be described as a front end portion, and a side on which the prism 51 is provided will be described as a rear end portion.

A side surface of the imaging element 53 that is in contact with an inner wall surface of the distal end fixing portion 35 is bonded to the inner wall surface of the distal end fixing portion 35 with an adhesive, and a rear end side of an assembly position of the prism 51 on the imaging element 53 is sealed with sealing resin 67.

Figure 3A:
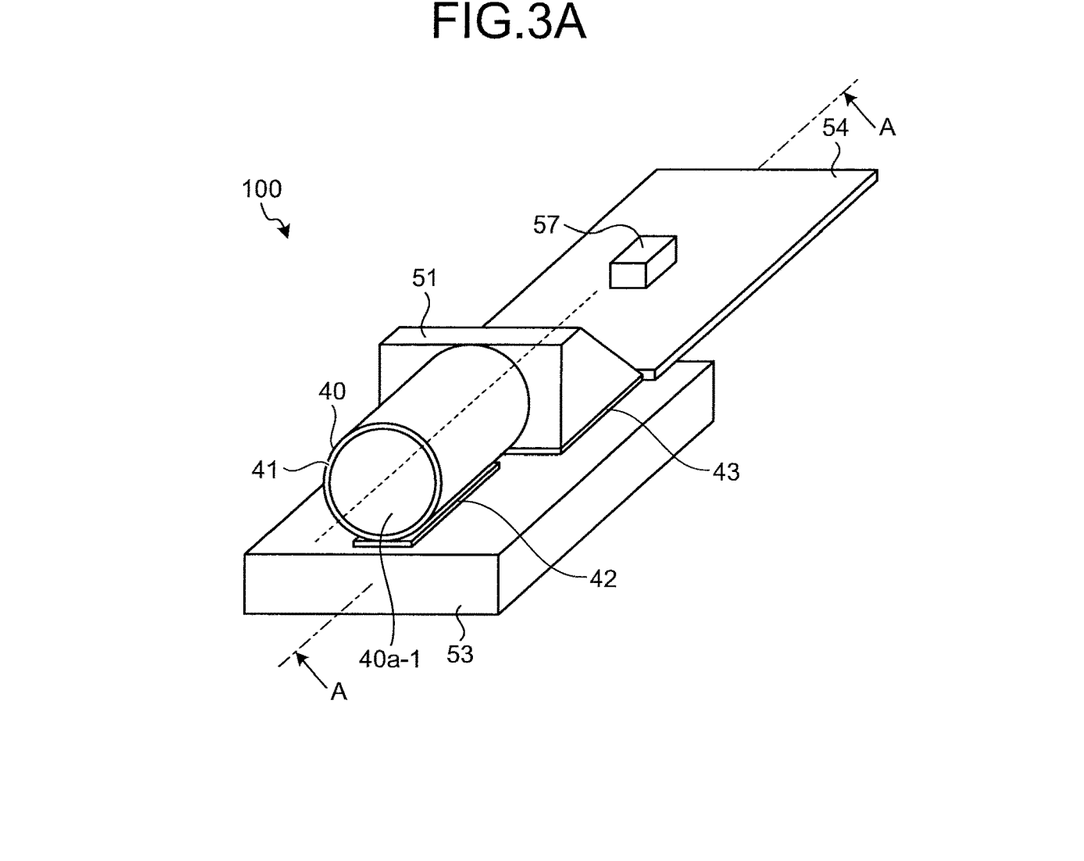
FIG. 3A is a perspective view of an imaging apparatus illustrated in FIG. 2.
Figure 3B:
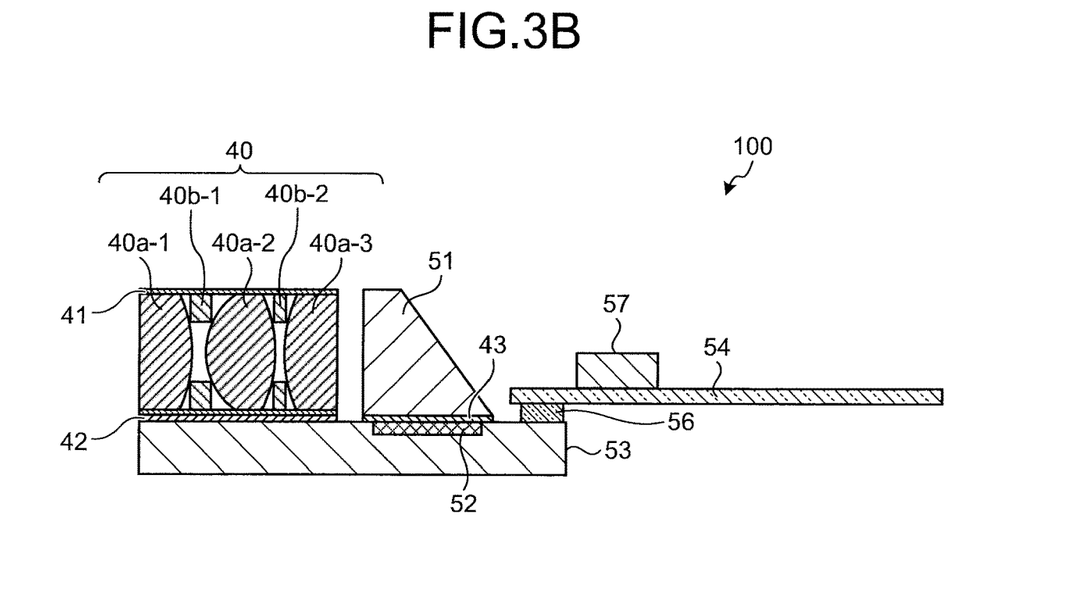
FIG. 3B is a cross-sectional view taken along a line A-A in FIG. 3A.

Next, the imaging apparatus 100 according to the first embodiment of the disclosure will be described. FIG. 3A is a perspective view of the imaging apparatus 100 illustrated in FIG. 2. FIG. 3B is a cross-sectional view taken along a line A-A in FIG. 3A.

As illustrated in FIG. 3A and FIG. 3B, in the imaging apparatus 100 according to the first embodiment of the disclosure, the lens unit 40 is connected onto a mounting region of the objective lenses 40a-1 to 40a-3 on the imaging element 53 via a lens adhesive 42, and the prism 51 is connected onto the light receiver 52 via a prism adhesive 43. A lens frame 41 of the lens unit 40 for holding the objective lenses 40a-1 to 40a-3 is directly mounted on a surface of the imaging element 53. An imaging element electrode 56 for connecting the flexible printed board 54 is provided on a rear end side of the imaging element 53.

The objective lenses 40a-1 to 40a-3, the spacers 40b-1 and 40b-2, and the diaphragm member (not illustrated) are inserted in the lens frame 41 to form the lens unit 40, and then the lens unit 40 is connected such that positions of the objective lenses 40a-1 to 40a-3 are determined by using the lens adhesive 42 provided on the principal surface of the imaging element 53 as a position determination unit. The lens unit 40 is moved to above the corresponding lens adhesive 42 while an upper side surface thereof is sucked by a jig or the like, the position of the lens unit 40 is then passively adjusted while the positions of the lens unit 40 and the lens adhesive 42 serving as a lens position determination unit are checked by a camera or the like from above, and thereafter the lens unit 40 is fixed to the imaging element 53. Similarly, the prism 51 is moved to above the corresponding prism adhesive 43 while an upper side surface thereof is sucked by a jig or the like, the position of the prism 51 is then adjusted while the positions of the prism 51 and the prism adhesive 43 serving as a prism position determination unit are checked by a camera or the like from above, and thereafter the prism 51 is fixed to the imaging element 53. To accurately perform positioning of the lens unit 40 and the prism 51, it is preferable to set the sizes of the lens adhesive 42 and the prism adhesive 43 to be approximately equal to or slightly greater than projection planes of the lens unit 40 and the prism 51 in the direction from above.

It may be possible to use the lens unit 40 in which the objective lenses 40a-1 to 40a-3 and the spacers 40b-1 and 40b-2 are integrated without using the lens frame 41. As the integration of the lens unit, the integration may be performed by applying an adhesive to connection surfaces of the objective lenses 40a-1 to 40a-3 or the spacers 40b-1 and 40b-2 in advance, putting the objective lens 40a-3, the spacer 40b-2, the objective lens 40a-2, the spacer 40b-1, and the objective lens 40a-1 in this order or the like in a frame member used for the integration, curing the adhesive, and taking the lens unit out of the frame member. When the lens frame 41 is not used as described above, the objective lenses 40a-1 to 40a-3 and the spacers 40b-1 and 40b-2 in circular external shapes may be cut at portions that are not used as optical paths for imaging, that is, what is called a D-cut may be performed. By performing the D-cut, a bonding area to be bonded to the imaging element 53 is increased, so that the objective lens can be fixed stably. Meanwhile, as a timing to perform the D-cut, it may be possible to perform the D-cut on each of the components before the components are put in place or it may be possible to collectively perform the D cut after the components are integrated, in the above-described generation steps. Furthermore, it is preferable to fill a periphery of a bonding portion between the lens unit 40 and the lens adhesive 42 with sealing resin (not illustrated) within a range in which the optical path is not obstructed, to thereby protect the bonding portion.

Next, a method for manufacturing the imaging apparatus 100 according to the first embodiment of the disclosure will be described. FIG. 4A to FIG. 4D are diagrams for explaining a process for manufacturing the imaging apparatus 100 illustrated in FIG. 2.

Figure 4A:
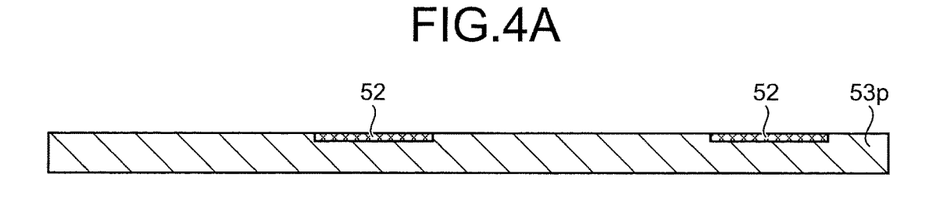
FIG. 4A is a diagram for explaining a process for manufacturing the imaging apparatus illustrated in FIG. 2.
Figure 4B:
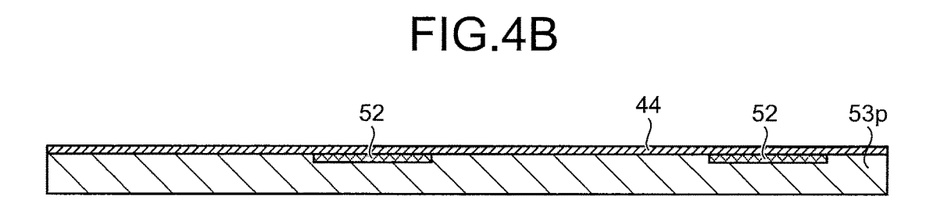
FIG. 4B is a diagram for explaining the process for manufacturing the imaging apparatus illustrated in FIG. 2.

An optical system adhesive layer 44 made with a photosensitive transparent adhesive is provided as illustrated in FIG. 4B on a wafer 53p on which the plurality of light receivers 52 are provided as illustrated in FIG. 4A. A plurality of imaging elements 53 are manufactured by dividing the wafer 53p into individual pieces through dicing such that the light receiver 52 and a lens mounting region are provided in a region of each of the imaging elements 53. The lens mounting region is a region in which the lens adhesive 42 is arranged, and the lens unit 40 is mounted in this region. A peripheral circuit for driving and controlling the imaging element 53 may be provided in the lens mounting region.

When an optical system adhesive layer 44 is made with a liquid photosensitive adhesive, the photosensitive adhesive is applied onto the wafer 53p by spin coating. After providing the photosensitive adhesive by spin coating, pre-baking is performed, so that the optical system adhesive layer 44 in a semi-cured state is obtained. This enables exposure and development, which makes it possible to perform patterning on the lens adhesive 42 and the prism adhesive 43. As the liquid photosensitive adhesive, for example, U-100 series of Taiyo Ink Mfg. Co., Ltd. may preferably be used.

When the optical system adhesive layer 44 is made with a film-shaped photosensitive adhesive, the film-shaped photosensitive adhesive is laminated on the wafer 53p. If the film-shaped photosensitive adhesive is used, it becomes possible to easily increase a thickness of the optical system adhesive layer 44. As the film-shaped photosensitive adhesive, for example, PerMX series of DuPont MRC Dry Film Ltd. and IBF series of Sumitomo Bakelite Co., Ltd. may preferably be used.

Figure 4C:
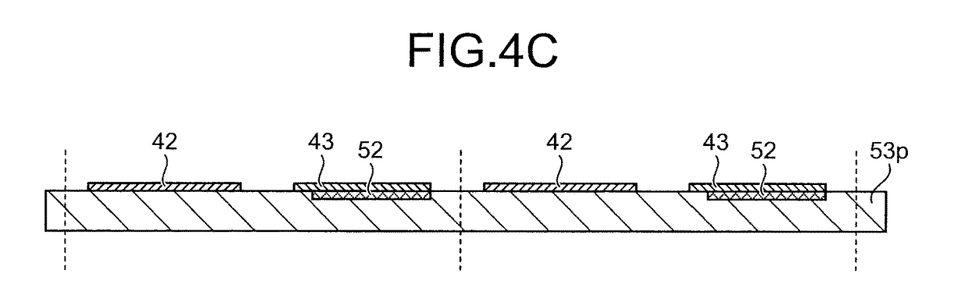
FIG. 4C is a diagram for explaining the process for manufacturing the imaging apparatus illustrated in FIG. 2.

After the optical system adhesive layer 44 is formed, patterning is performed on the optical system adhesive layer 44 through a photolithography process to form the lens adhesive 42 and the prism adhesive 43 as illustrated in FIG. 4C, and dicing is performed at positions indicated by dotted lines in FIG. 4C to obtain the divided individual imaging elements 53.

Figure 4D:
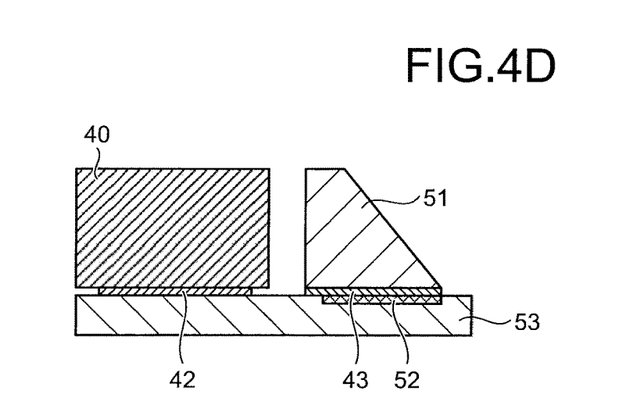
FIG. 4D is a diagram for explaining the process for manufacturing the imaging apparatus illustrated in FIG. 2.

Thereafter, positions of the lens unit 40 and the prism 51 are determined by using the lens adhesive 42 and the prism adhesive 43 as the position determination unit, and the lens unit 40 and the prism 51 are respectively connected to the lens adhesive 42 and the prism adhesive 43 through application of heat and pressure. The lens unit 40 and the prism 51 are temporarily fixed, and thereafter, the lens unit 40 and the prism 51 may be connected simultaneously or separately depending on adhesiveness of the adhesives. When the lens unit 40 and the prism 51 are connected separately, it may be possible to first connect the prism 51 with the prism adhesive 43, and then adjust a connection position of the lens unit 40 with monitoring of an image output by the imaging element 53.

The imaging apparatus 100 can be miniaturized by directly connecting, to the imaging element 53, the lens frame 41 of the lens unit 40 or an integrated lens unit in which a lens frame is not used. However, to accurately perform positioning while adjusting the optical axes of the lens unit 40 and the prism 51 to match each other, it is necessary to accurately control an application amount or an application position of an adhesive to be used, and, it has not been easy to manufacture an imaging apparatus in which the lens unit 40 is directly connected to the imaging element 53 with high accuracy. The imaging element 53 used in the imaging apparatus 100 according to the first embodiment of the disclosure is obtained such that a photosensitive transparent adhesive is applied at a wafer level on which the plurality of light receivers 52 are provided, patterning is performed on the photosensitive adhesive through a photolithography process to form the lens adhesive 42 and the prism adhesive 43, and then the wafer is divided into individual pieces. In the first embodiment of the disclosure, the lens adhesive 42 and the prism adhesive 43 are formed through the photolithography process, that is, through exposure and development using a photomask; therefore, it is possible to control relative arrangement positions of the lens adhesive 42 and the prism adhesive 43 in a planar direction with high accuracy.

Furthermore, when a liquid adhesive is used as the photosensitive adhesive, it is possible to control a thickness of the adhesive with high accuracy by spin coating, and, even when the film-shaped photosensitive adhesive is used, it is possible to control a thickness of the film with high accuracy in a film manufacturing process; therefore, it is possible to adjust the optical axis of the lens unit 40 and the optical axis of the prism 51 to match each other with high accuracy by controlling thicknesses of the lens adhesive 42 and the prism adhesive 43 with high accuracy. In the first embodiment of the disclosure, the thickness of the lens adhesive 42 and the thickness of the prism adhesive 43 become approximately equal to each other both when the liquid photosensitive adhesive is used and when the film-shaped photosensitive adhesive is used.

In the first embodiment of the disclosure, the connection positions of the lens unit 40 and the prism 51 are determined by using the lens adhesive 42 and the prism adhesive 43, which are formed as described above, as position determination members; therefore, it is possible to obtain the imaging apparatus 100 in which positioning can be performed with high accuracy and which can be miniaturized.

Meanwhile, in the first embodiment of the disclosure, the imaging element is a transverse-mount type in which the principal surface, on which the light receiver is provided, is arranged parallel (horizontally) to the optical axis of the objective lens; however, it may be possible to use an imaging element of a vertical-mount type in which light is directly input from an objective lens to a light receiver without using a prism. When an imaging element of a transverse-mount type is used, it is possible to obtain a miniaturized high-precision imaging apparatus by forming a lens adhesive on the light receiver through a photolithography process and connecting the lens unit while determining a position of the lens unit by using the formed lens adhesive as a position determination unit.

Second Embodiment

Figure 5A:
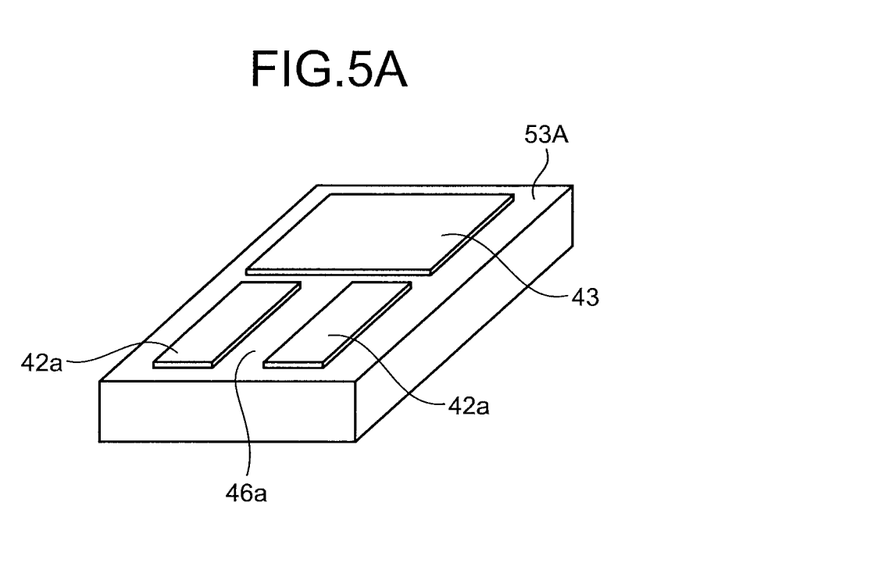
FIG. 5A is a perspective view for explaining an imaging element used in an imaging apparatus according to a second embodiment of the disclosure.
Figure 5B:
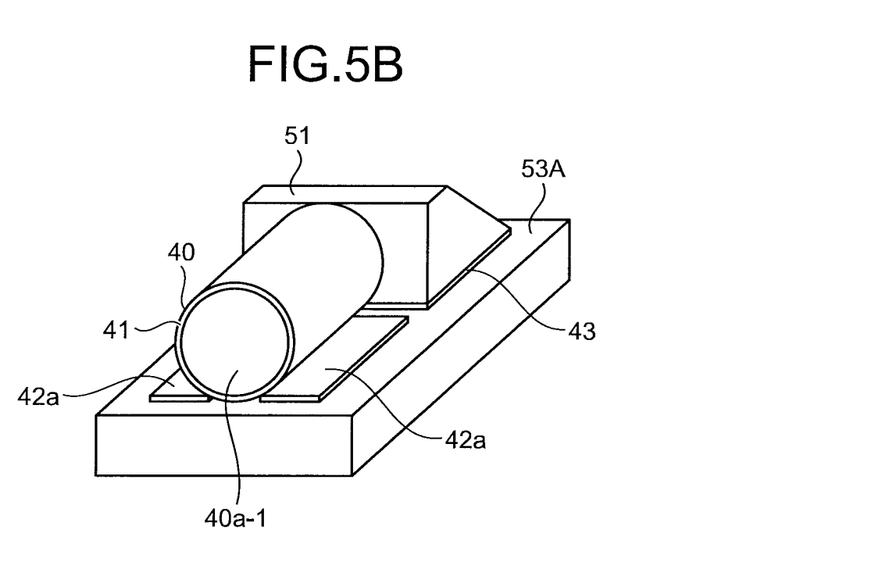
FIG. 5B is a perspective view for explaining the imaging apparatus according to the second embodiment of the disclosure.

FIG. 5A is a perspective view for explaining an imaging element used in an imaging apparatus according to a second embodiment of the disclosure. FIG. 5B is a perspective view for explaining the imaging apparatus according to the second embodiment of the disclosure. In FIG. 5A and FIG. 5B, illustration of an imaging element electrode is omitted.

Lens adhesives 42a are provided in two rows parallel to the optical axes of the objective lenses 40a-1 to 40a-3, on a principal surface of an imaging element 53A used in the imaging apparatus according to the second embodiment of the disclosure. The lens adhesives 42a in the two rows and the principal surface of the imaging element 53A constitute a groove 46a, and a connection position of the lens unit 40 is determined by arranging the lens unit 40 in the groove 46a. A position of the lens unit 40 in a direction perpendicular to an optical axis direction is automatically determined by arranging the lens adhesives 42a with high accuracy, and it is sufficient to perform adjustment in the optical axis direction and in a rotation direction. To determine the position of the lens unit 40 in the optical axis direction with high accuracy, it is preferable to set lengths of the lens adhesives 42a in the optical axis direction and a length of the lens unit 40 in the optical axis direction to be approximately equal to each other.

In the second embodiment of the disclosure, it is possible to simplify adjustment in positioning of the lens unit 40, and simplify adjustment of a height of the lens unit 40 due to contraction at the time of curing the lens adhesives 42a because the lens adhesive 42a is not provided between the lens unit 40 and the principal surface of the imaging element 53A in the groove 46a. Furthermore, it is preferable to fill a periphery of a bonding portion between the lens unit 40 and the lens adhesives 42a with sealing resin (not illustrated) within a range in which the optical path is not obstructed, to thereby protect the bonding portion.

Figure 6A:
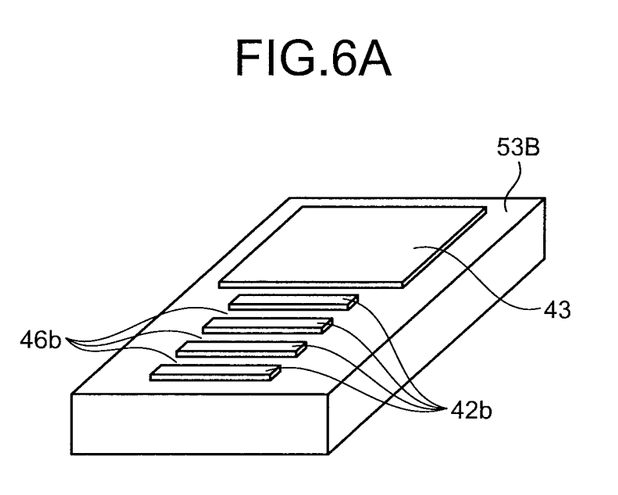
FIG. 6A is a perspective view for explaining an imaging element used in an imaging apparatus according to a first modification of the second embodiment of the disclosure.
Figure 6B:
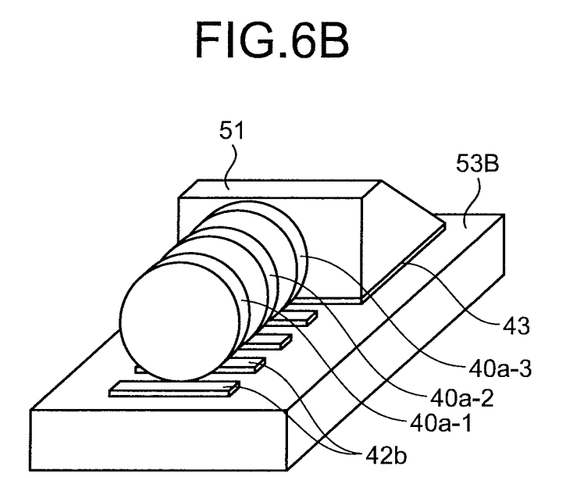
FIG. 6B is a perspective view for explaining the imaging apparatus according to the first modification of the second embodiment of the disclosure.

Moreover, it may be possible to provide a plurality of lens adhesives on the principal surface of the imaging element in a plurality of directions perpendicular to the optical axes of the objective lenses 40a-1 to 40a-3. FIG. 6A is a perspective view for explaining an imaging element used in an imaging apparatus according to a first modification of the second embodiment of the disclosure. FIG. 6B is a perspective view for explaining the imaging apparatus according to the first modification of the second embodiment of the disclosure. In FIG. 6A and FIG. 6B, illustration of an imaging element electrode is omitted.

Lens adhesives 42b are provided in four rows in a direction perpendicular to the optical axes of the objective lenses 40a-1 to 40a-3 on a principal surface of an imaging element 53B used in the imaging apparatus according to the first modification of the second embodiment of the disclosure. The lens adhesives 42b in the four rows and the principal surface of the imaging element 53B constitute grooves 46b, and positions of the objective lenses 40a-1 to 40a-3 are determined by arranging each of the objective lenses 40a-1 to 40a-3 in the respective grooves 46b. It is preferable to adjust arrangement intervals of the lens adhesives 42b in accordance with the maximum length of the objective lenses 40a-1 to 40a-3 in the optical axis direction. Positions of the objective lenses 40a-1 to 40a-3 in the optical axis direction are automatically determined by arranging the lens adhesives 42b with high accuracy, and it is sufficient to perform adjustment in the direction perpendicular to the optical axis direction and in a rotation direction. To determine the positions of the objective lenses 40a-1 to 40a-3 in the direction perpendicular to the optical axis with high accuracy, it is preferable to set lengths of the lens adhesives 42b in the direction perpendicular to the optical axis direction and the lengths of the objective lenses 40a-1 to 40a-3 in the direction perpendicular to the optical axis direction to be approximately equal to each other. Furthermore, it is preferable to fill a periphery of a bonding portion between the objective lenses 40a-1 to 40a-3 and the lens adhesives 42b with sealing resin (not illustrated) within a range in which the optical path is not obstructed, to thereby protect the bonding portion.

Figure 7A:
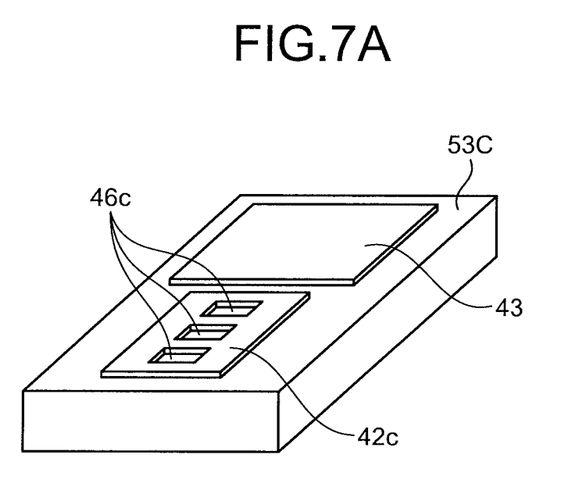
FIG. 7A is a perspective view for explaining an imaging element used in an imaging apparatus according to a second modification of the second embodiment of the disclosure.
Figure 7B:
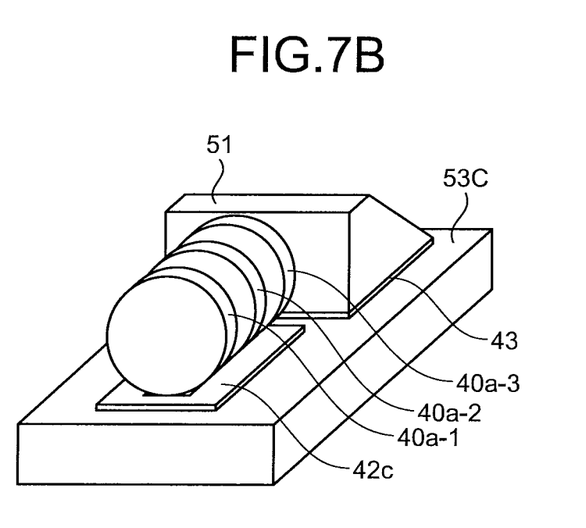
FIG. 7B is a perspective view for explaining the imaging apparatus according to the second modification of the second embodiment of the disclosure.

Moreover, it may be possible to provide grooves for arranging the respective objective lenses 40a-1 to 40a-3 on lens adhesives provided on the principal surface of the imaging element. FIG. 7A is a perspective view for explaining an imaging element used in an imaging apparatus according to a second modification of the second embodiment of the disclosure. FIG. 7B is a perspective view for explaining the imaging apparatus according to the second modification of the second embodiment of the disclosure. In FIG. 7A and FIG. 7B, illustration of an imaging element electrode is omitted.

A lens adhesive 42c is provided on a principal surface of an imaging element 53C used in the imaging apparatus according to the second modification of the second embodiment of the disclosure, and grooves 46c are provided in three rows on the lens adhesive 42c in a direction perpendicular to the optical axes of the objective lenses 40a-1 to 40a-3. The grooves 46c are formed by removing the lens adhesive 42c through exposure and development, and positions of the objective lenses 40a-1 to 40a-3 are determined by arranging each of the objective lenses 40a-1 to 40a-3 in the respective grooves 46c. It is preferable to adjust arrangement intervals of the grooves 46c in accordance with thicknesses of the objective lenses 40a-1 to 40a-3. Furthermore, it is preferable to set lengths and widths of the grooves 46c such that end portions of the grooves 46c on the principal surface side come in contact with the objective lenses 40a-1 to 40a-3 to allow for positioning when the objective lenses 40a-1 to 40a-3 are arranged. Positions of the objective lenses 40a-1 to 40a-3 in the optical axis direction and in the direction perpendicular to the optical axis are automatically determined by arranging the lens adhesive 42c through the photolithography process with high accuracy, and it is sufficient to perform adjustment in a rotation direction.

Moreover, it is preferable to fill a periphery of a bonding portion between the objective lenses 40a-1 to 40a-3 and the lens adhesive 42c with sealing resin (not illustrated) within a range in which the optical path is not obstructed, to thereby protect the bonding portion.

Third Embodiment

Figure 8A:
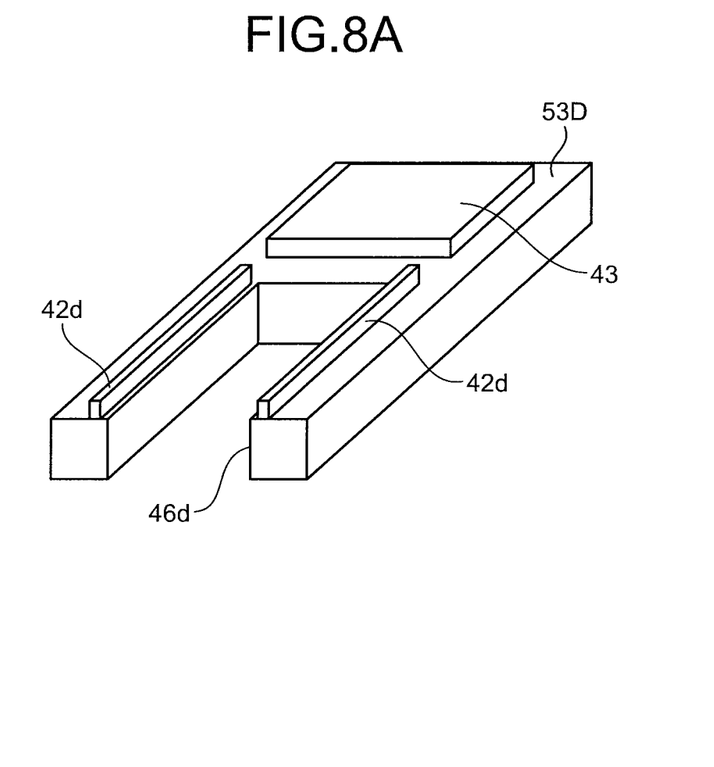
FIG. 8A is a perspective view for explaining an imaging element used in an imaging apparatus according to a third embodiment of the disclosure.
Figure 8B:
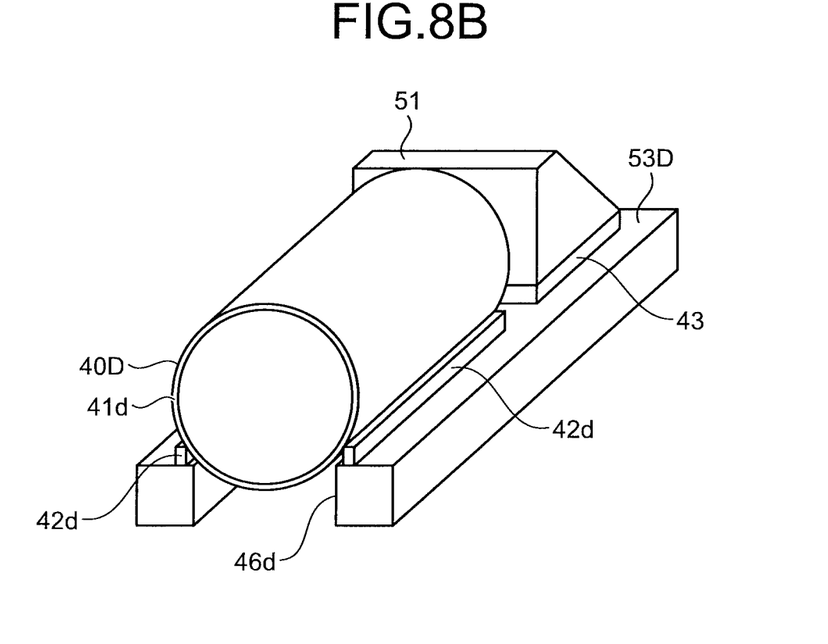
FIG. 8B is a perspective view for explaining the imaging apparatus according to the third embodiment of the disclosure.
Figure 8C:
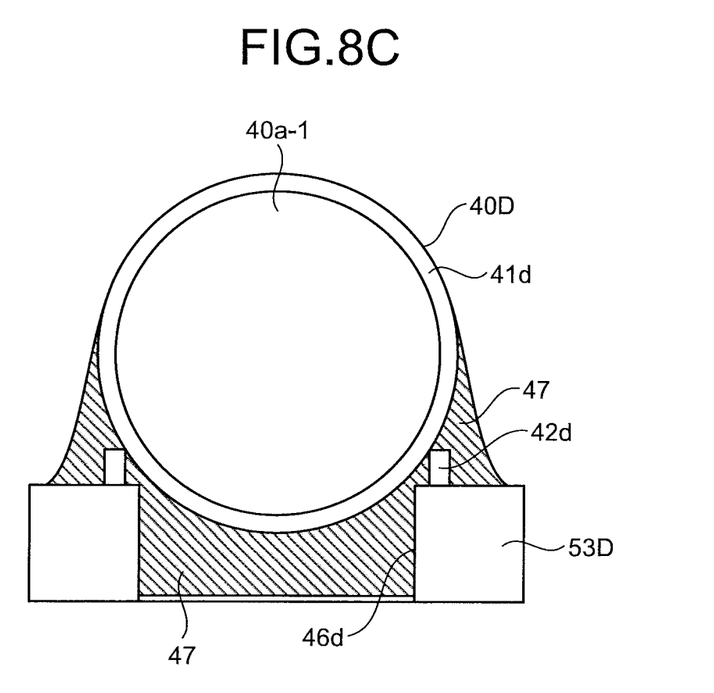
FIG. 8C is a diagram of the imaging apparatus illustrated in FIG. 8B, viewed from a front end portion.

FIG. 8A is a perspective view for explaining an imaging element used in an imaging apparatus according to a third embodiment of the disclosure. FIG. 8B is a perspective view for explaining the imaging apparatus according to the third embodiment of the disclosure. FIG. 8C is a diagram of the imaging apparatus illustrated in FIG. 8B, viewed from a front end portion. In FIG. 8A and FIG. 8B, illustration of an imaging element electrode is omitted.

Lens adhesives 42d are provided in two rows parallel to an optical axis of a lens unit 40D, on a principal surface of an imaging element 53D used in the imaging apparatus according to the third embodiment of the disclosure. Furthermore, a groove 46d for arranging the lens unit 40D is provided between the lens adhesives 42d in the two rows.

To miniaturize the imaging apparatus, a diameter of an objective lens to be used is limited; however, in the third embodiment of the disclosure, the groove 46d is formed on the imaging element 53D and the lens unit 40D is arranged so as to be put in the groove 46d, so that it becomes possible to use the lens unit 40D with a large-diameter objective lens while miniaturizing the imaging apparatus. With this configuration, it becomes possible to acquire a bright image.

The groove 46d may be formed by performing crystal anisotropic wet etching, deep reactive-ion etching, or processing using a dicing blade on the imaging element 53D made of silicon. It is preferable to set a length of the groove 46d in the optical axis direction to be approximately equal to a length of the lens unit 40D, and it is preferable to determine a length of the groove 46d in a direction perpendicular to the optical axis direction by taking into account the diameter of the lens unit 40D and a position of the optical axis. Positions of the lens unit 40D in the optical axis direction and in the direction perpendicular to the optical axis direction are automatically determined by arranging the lens unit 40D so as to be put in the groove 46d, and it is sufficient to perform adjustment in a rotation direction.

An outer circumference of the lens unit 40D may come in contact with the groove 46d; however, it is preferable to hold the lens unit 40D only by the lens adhesives 42d without contact with the groove 46d as illustrated in FIG. 8C. A position of the lens unit 40D can be determined with high accuracy by holding the lens unit 40D only by contact with the lens adhesives 42d because position accuracy of the lens adhesives 42d is higher than position accuracy of the groove 46d. Furthermore, it is preferable to fill a periphery of a bonding portion between the lens unit 40D and the lens adhesives 42d with sealing resin 47 within a range in which the optical path is not obstructed, to thereby protect the bonding portion.

Figure 9A:
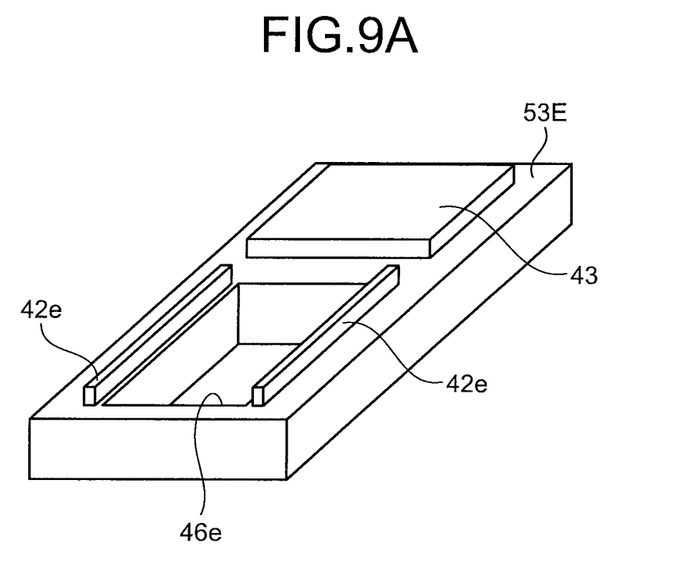
FIG. 9A is a perspective view for explaining an imaging element used in an imaging apparatus according to a first modification of the third embodiment of the disclosure.

A groove may include an opening on one side thereof, or may not include an opening. FIG. 9A is a perspective view for explaining an imaging element used in an imaging apparatus according to a first modification of the third embodiment of the disclosure. In FIG. 9A, illustration of an imaging element electrode is omitted. On a principal surface of an imaging element 53E, lens adhesives 42e are provided in two rows parallel to an optical axis of a lens unit, and a groove 46e without an opening on a front end side of the imaging element 53E is provided between the lens adhesives 42e in the two rows. By putting the lens unit in the groove 46e to facilitate positioning, it becomes possible to obtain a miniaturized high-precision imaging apparatus.

Figure 9B:
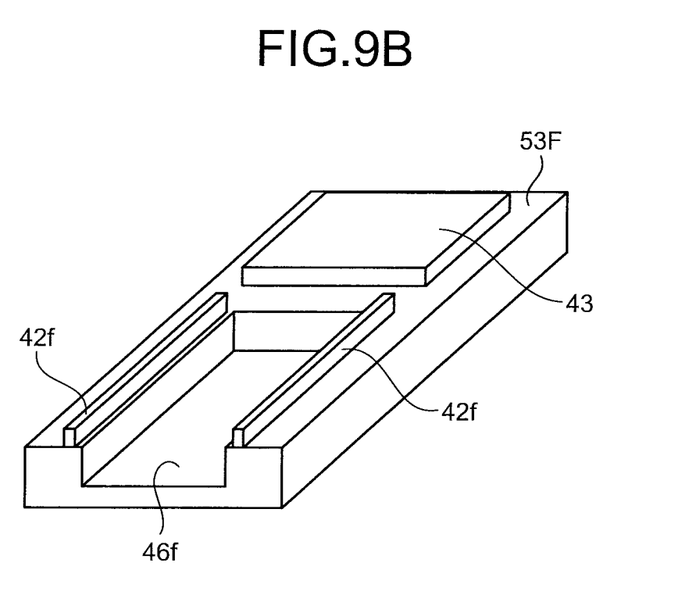
FIG. 9B is a perspective view for explaining an imaging element used in an imaging apparatus according to a second modification of the third embodiment of the disclosure.

Furthermore, a groove may include a closed-bottom. FIG. 9B is a perspective view for explaining an imaging element used in an imaging apparatus according to a second modification of the third embodiment of the disclosure. In FIG. 9B, illustration of an imaging element electrode is omitted. On a principal surface of an imaging element 53F, lens adhesives 42f are provided in two rows parallel to an optical axis of a lens unit, and a groove 46f with a closed-bottom is provided between the lens adhesives 42f in the two rows. By putting the lens unit in the groove 46f to facilitate positioning, it becomes possible to obtain a miniaturized high-precision imaging apparatus.

Figure 9C:
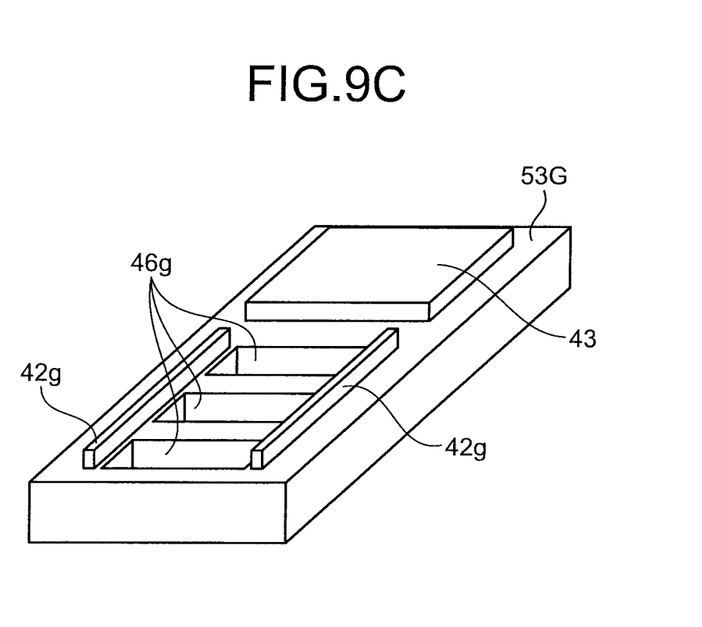
FIG. 9C is a perspective view for explaining an imaging element used in an imaging apparatus according to a third modification of the third embodiment of the disclosure.

Moreover, it may be possible to provide a plurality of grooves in accordance with objective lenses. FIG. 9C is a perspective view for explaining an imaging element used in an imaging apparatus according to a third modification of the third embodiment of the disclosure. In FIG. 9C, illustration of an imaging element electrode is omitted. On a principal surface of an imaging element 53G, lens adhesives 42g are provided in two rows parallel to an optical axis of a lens unit, and three grooves 46g for arranging the objective lenses 40a-1 to 40a-3 are provided between the lens adhesives 42g in the two rows. By putting each of the objective lenses 40a-1 to 40a-3 in the respective grooves 46g to facilitate positioning, it is possible to obtain a miniaturized high-precision imaging apparatus.

According to some embodiments, an objective lens is directly mounted on a surface of an imaging element; therefore, it is possible to miniaturize an imaging apparatus.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
   an optical system configured to collect incident light, the optical system including:
      a plurality of objective lenses; and
      a prism configured to reflect light collected by the plurality of objective lenses;
   an image sensor including a light receiver surface configured to receive the reflected light and perform photoelectric conversion to generate an electrical signal; and
   an optical system adhesive layer configured to bond the optical system to a principal surface of the image sensor where the light receiver surface is provided, wherein
   the optical system adhesive layer is a photosensitive transparent adhesive for which patterning is performed through a photolithography process, the optical system adhesive layer being configured to determine a position of the optical system relative to the light receiver surface,
   the image sensor is arranged such that the principal surface is parallel to optical axes of the plurality of objective lenses,
   the optical system adhesive layer includes:
      a prism adhesive configured to bond the prism to the light receiver surface: and
      lens adhesives configured to bond the plurality of objective lenses to a lens mounting region, wherein a thickness of the prism adhesive is equal to a thickness of the lens adhesives and
      the lens adhesives are provided in a direction parallel to the optical axes of the plurality of objective lenses or in a direction perpendicular to the optical axes of the plurality of objective lenses, the plurality of objective lenses being arranged between the lens adhesives, to thereby determine positions of the plurality of object lenses.

2. The imaging apparatus according to claim 1, wherein the lens adhesives are provided in two rows parallel to the optical axes of each the plurality of objective lenses, and allow the plurality of objective lenses held by a lens frame to be arranged in a groove formed by the lens adhesives in the two rows and the principal surface of the image sensor, to thereby determine the positions of the plurality of objective lenses.

3. The imaging apparatus according to claim 2, wherein the lens adhesives are not provided between the principal surface of the image sensor and the lens frame or between the principal surface of the image sensor and the plurality of objective lenses.

4. The imaging apparatus according to claim 1, wherein the lens adhesives are provided in flail the direction perpendicular to the optical axes of the plurality of objective lenses, and allow each of the plurality of objective lenses to be arranged in respective grooves formed by the lens adhesives and the principal surface of the image sensor, to thereby determine the positions of the plurality of objective lenses.

5. The imaging apparatus according to claim 4, wherein the lens adhesives are not provided between the principal surface of the image sensor and a lens frame configured to hold the objective lenses frames or between the principal surface of the image sensor and the objective lenses.

6. The imaging apparatus according to claim 1, wherein the lens adhesives are provided in two rows parallel to the optical axes of the plurality of objective lenses, and
   the image sensor includes a groove provided between the lens adhesives in the two rows, and allows the plurality of objective lenses to be arranged between the lens adhesives in the two rows, to thereby determine the positions of the plurality of objective lenses.

7. The imaging apparatus according to claim 6, further comprising a lens frame configured to hold the plurality of objective lenses, the lens frame being held by the lens adhesives without coming into contact with the image sensor,
   wherein peripheries of bonding portions between the lens frame and the lens adhesives are filled with sealing resin.

8. The imaging apparatus according to claim 1, wherein the lens adhesives are provided in two rows parallel to the optical axes of the plurality of objective lenses, and
   the image sensor includes a plurality of grooves provided between the lens adhesives so as to be perpendicular to the optical axes of the plurality of objective lenses, and allows each of the plurality of objective lenses to be arranged in the respective grooves, to thereby determine the positions of the plurality of objective lenses.

9. An endoscopic system configured to be inserted in a living body and capture an image of an inside of the living body, the endoscopic system comprising:
   an endoscope including the imaging apparatus according to claim 1 at a distal end portion of the endoscope.

10. An imaging apparatus manufacturing method comprising:

forming a layer of an optical system adhesive layer made of a photosensitive transparent adhesive on a wafer where a plurality of light receiver surfaces are provided, the plurality of light receiver surfaces being each configured to receive light and perform photoelectric conversion to generate an electrical signal:

performing patterning on a portion of the optical system adhesive layer through a photolithography process to form a pattern of a plurality of lens adhesives and a plurality of prism adhesives;

performing dicing on the wafer to obtain a plurality of individual image sensors, each of the image sensors having a lens adhesives of the plurality of lens adhesives and a prism adhesive of the plurality of prism adhesives;

determining a position of an optical system having objective lenses on each individual. image sensor by arranging the optical. system between the lens adhesives; and connecting the optical system onto each individual image sensor by bonding the optical system between the lens adhesives and bonding a prism configured to reflect light collected by the objective lenses to the image sensor via the prism adhesive;

wherein the lens adhesives is formed in a direction parallel to optical axes of the objective lenses or in a direction perpendicular to the optical axes of the objective lenses.

11. The imaging apparatus manufacturing method according to claim 10, wherein the forming of the layer of the optical system adhesive layer includes forming a liquid photosensitive adhesive on the wafer by spin coating.

12. The imaging apparatus manufacturing method according to claim 10, wherein the forming of the layer of the optical system adhesive layer includes laminating a film-shaped photosensitive adhesive on the wafer.

* * * * *